United States Patent [19]

Guigan

[11] Patent Number: 4,673,653
[45] Date of Patent: Jun. 16, 1987

[54] METHOD OF PERFORMING BIOLOGICAL ANALYSES USING IMMUNOLOGICAL REACTIONS, AND APPARATUS FOR PERFORMING THE METHOD

[76] Inventor: Jean Guigan, 9, rue Jean Mermoz, 75008 Paris, France

[21] Appl. No.: 840,613

[22] Filed: Mar. 17, 1986

[30] Foreign Application Priority Data

Mar. 26, 1985 [FR] France ................................ 85 04476

[51] Int. Cl.⁴ .................... G01N 31/00; G01N 33/549
[52] U.S. Cl. .......................................... 436/8; 422/56; 422/64; 422/58; 436/532
[58] Field of Search .................................... 422/55–58, 422/64; 436/531, 532, 517, 8–19

[56] References Cited

U.S. PATENT DOCUMENTS 3,843,450  8/1974  Saxholm ................................ 422/58
4,045,179  8/1977  Bunce ................................... 422/58
4,138,474  2/1979  Updike ................................. 422/58

Primary Examiner—Deborah L. Kyle
Assistant Examiner—T. J. Waller
Attorney, Agent, or Firm—Sughrue, Mion, Zinn, Macpeak, and Seas

[57] ABSTRACT

A method of performing biological analysis of a liquid sample using a one-piece plastic container (1), said container being compartmented to provide a storage chamber (4) for the sample, a calibrated cell (6), and a plurality of storage chambers (30, 40, 50) for various liquids such as a conjugate liquid, a substrate liquid, and a blocking liquid. A succession of centrifuging operations serve to successively pass the sample and said liquids into a reaction vat (11) containing a bead (17) which is initially covered in antigens or antibodies. Means are also provided for rinsing the bead (17).

2 Claims, 20 Drawing Figures

METHOD OF PERFORMING BIOLOGICAL ANALYSES USING IMMUNOLOGICAL REACTIONS, AND APPARATUS FOR PERFORMING THE METHOD

The present invention relates to a method of performing biological analyses using immunological reactions on solid media, and to apparatus for performing the method.

BACKGROUND OF THE INVENTION

It is well known that such analyses requires an operator to perform numerous manipulations, such as transfers between test tubes, and as a result there are risks of contamination.

The aim of the present invention is to provide a method which is capable of being entirely automated and which may be used very simply by medical practitioners themselves in their own consulting rooms or offices.

SUMMARY OF THE INVENTION

The present invention provides a method of performing biological analyses using immunological reactions on a liquid sample, the method comprising the steps of:
providing a container which is closed by a lid, said container having compartments to define:
a storage chamber for said liquid sample, said storage chamber being connected by a capillary duct to one end of a calibrated cell whose other end is connected via a capillary duct to an overflow chamber;
a plurality of liquid storage chambers, for storing liquids such as a conjugate liquid, a substrate liquid, and a blocking liquid, said liquid storage chambers being disposed around a pouring chamber, said pouring chamber being connected to each of said liquid storage chambers and to said calibrated cell via respective capillary ducts extending in various directions, said pouring chamber also communicating with a reaction vat via a spout preventing liquid from returning from said reaction vat to said pouring chamber;
a liquid drain tank communicating with said reaction vat; and
a bead fixed in said reaction vat and suitable for being covered with antigens or antibodies;
said lid being provided with:
an insertion receptacle for receiving a sample and communicating directly with said sample storage chamber, said insertion receptacle being situated above said sample storage chamber; and
a removable stopper penetrating into said pouring chamber to close the ends of said capillary ducts leading thereto; and a closable opening communicating directly with said reaction vat to enable a cleaning liquid to be inserted therein;
means being provided for positioning said container on the periphery of a turntable in a plurality of different predetermined positions, which positions differ from one another by said container being rotated about its own axis through a given angle relative to said turntable;
said conjugate liquid, said substrate liquid, and said blocking liquid being initially disposed in respective ones of said liquid storage chambers;
said sample being inserted into said sample insertion receptacle, and flowing therefrom under gravity into said sample storage chamber;
said stopper being removed;
said container being placed on said turntable in order to perform a plurality of successive centrifuging operations, with the angular position of said container being selected each time from said predetermined angular position as a function of the orientation of the capillary duct concerned relative to the direction of centrifugal force in such a manner as to perform the following sequence of operations:
passing said sample from said storage chamber into said calibrated cell;
passing said sample from said calibrated cell into said reaction vat;
eliminating surplus sample which is not fixed on said bead to said drain tank;
inserting said flushing liquid into said reaction vat to clean said bead a first time, then eliminating said liquid to said drain tank;
inserting said conjugate liquid into said reaction vat via said pouring chamber;
eliminating surplus conjugate liquid which is not fixed on said bead into said drain tank;
inserting said flushing liquid into said reaction vat to clean said bead a second time and eliminating said liquid to said drain tank;
inserting said substrate liquid into said reaction vat via said pouring chamber;
eliminating surplus substrate liquid which is not fixed on said lead into said drain tank;
inserting said blocking liquid into said reaction vat via said pouring chamber; and
then reading the reaction on said bead by optical analysis means.

The reaction with the bead may be observed by any suitable means, for example a photometer situated above the lid of said container.

In a preferred implementation said predetermined positions of said container are at substantially the following angles from one another: 60°; 90°; 180°; and 270°; with said capillary ducts leading to said pouring chamber being substantially at said angles from one another.

The present invention also provides apparatus for performing the above method, said apparatus comprising a flat cylindrical container of transparent plastic material and closed by a lid of transparent plastic material, said container being molded as a single part having compartments to define:
a storage chamber for said liquid sample, said storage chamber being connected by a capillary duct to one end of a calibrated cell whose other end is connected via a capillary duct to an overflow chamber;
a plurality of liquid storage chambers, for storing liquids such as a conjugate liquid, a substrate liquid, and a blocking liquid, said liquid storage chambers being disposed around a pouring chamber, said pouring chamber being connected to each of said liquid storage chambers and to said calibrated cell via respective capillary ducts extending in various directions, said pouring chamber also communicating with a reaction vat via a spout preventing liquid from returning from said reaction vat to said pouring chamber;

a liquid drain tank communicating with said reaction vat; and a bead fixed in said reaction vat and suitable for being covered with antigens or antibodies;

said lid being provided with:

an insertion receptacle for receiving a sample and communicating directly with said sampled storage chamber, said insertion receptacle being situated above said sample storage chamber;

a closable opening situated above said reaction vat for receiving said flushing liquid; and a chimney situated above said pouring chamber and intended to receive a stopper suitable for closing all of the orifices opening out into said pouring chamber, said chimney together with said container and said lid constituting a one-piece part of molded plastic material.

In a particularly advantageous embodiment the capillary ducts making two of said liquid storage chambers communicate with said pouring chamber being diametrically opposed about the pouring chamber, and said ducts are at respective angles of substantially 60° and 120° with the capillary duct putting said third liquid storage chamber into communication with said pouring chamber.

Advantageously said pouring chamber includes internal ribs constituting deflectors to prevent a liquid while being expelled from one of said liquid storage chambers from penetrating into another of said liquid storage chambers.

Said liquid storage chambers may include internal ribs for partially subdividing said chambers, said ribs being suitable for breaking the slope taken up by the liquid during the various centrifuging operations.

The essential advantage of the method is that it is capable of being fully automated under the control of an electronic system which runs all the steps in order and then interprets the results.

BRIEF DESCRIPTION OF THE DRAWINGS

An embodiment of the invention is described by way of example with reference to the accompanying drawings, in which.

MORE DETAILED DESCRIPTION

Figure 1:
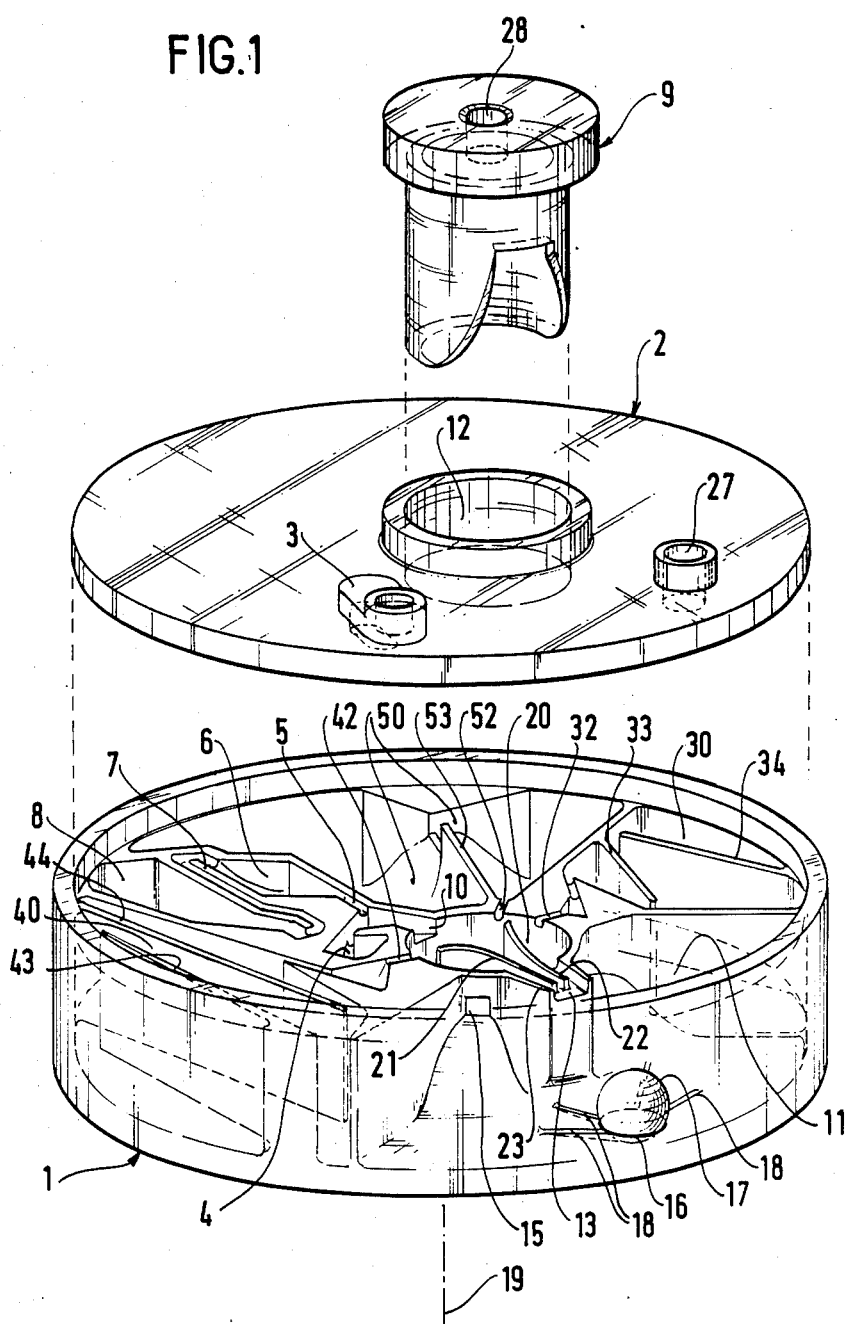
FIG. 1 is an exploded perspective view of apparatus for performing the method in accordance with the invention.
Figure 2:
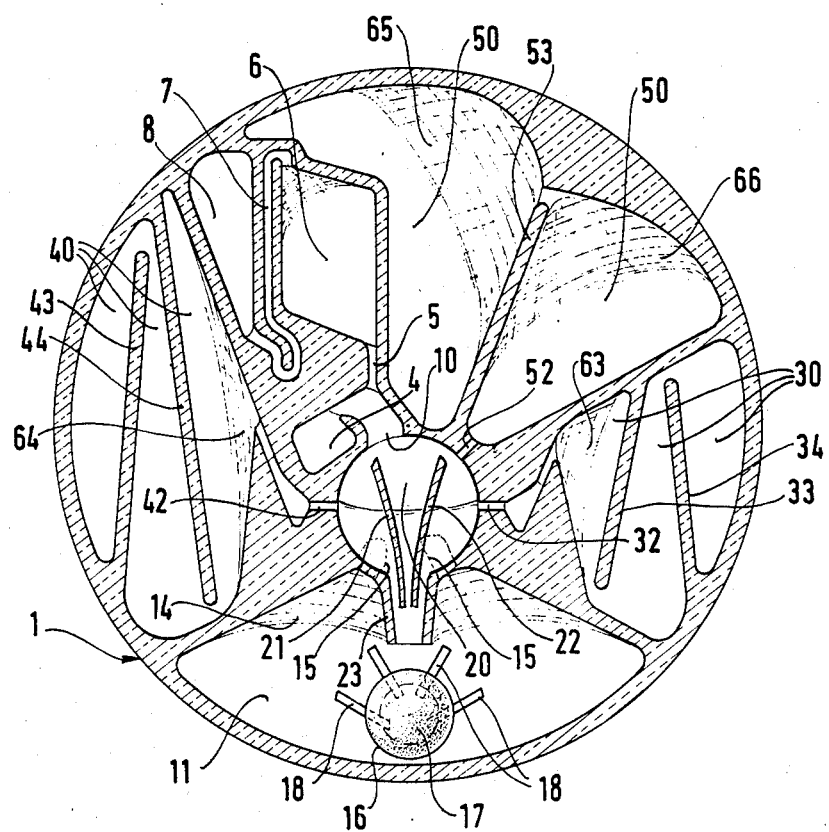
FIG. 2 is a section view through the apparatus, seen from above.

FIGS. 1 and 2 show a generally flat cylindrical container 1 which is closed by a lid 2 of plastic material, e.g. by hot welding. By way of example, the container may have a diameter of about 35 millimeters and it may be about 7 millimeters high.

The top of the lid 2 includes an insertion receptacle 3 for receiving a liquid sample and communicating directly with a chamber 4 for storing the sample inside the container.

The storage chamber 4 is connected by a capillary duct 5 to a calibrated cell 6 which communicates via a capillary duct 7 with an overflow chamber 8, and via an orifice 10 with a pouring chamber 20. The pouring chamber 20 communicates with a reaction vat 11 via a spout 23 which, together with the lid 2 defines an orifice 13. The level of the spout is such that it allows liquid to flow from the pouring chamber 20 into the reaction vat 11 while preventing liquid from flowing in the opposite direction, even during centrifuging. The pouring chamber is provided with deflector ribs 21 and 22 which guide the liquid leaving various chambers towards the reaction vat 11.

On its pouring chamber side the reaction vat has a sloping wall 14 with orifices 15 at its top communicating with an internal liquid drain tank. The bottom of the reaction vat 11 includes a depression 16 in the form of a spherical cap suitable for receiving a bead 17. A plurality of grooves 18 lead in a generally radial direction towards the depression 16. By way of example, the bead may be 6 mm in diameter.

The container further includes three liquid storage chambers:

a storage chamber 30 for a conjugate liquid 31 communicating with the pouring chamber 20 via a capillary duct 32 and partially subdivided by internal walls 33 and 34;

a storage chamber 40 for a substrate liquid 41, communicating with the pouring chamber 20 via a capillary duct 42 and partially subdivided by internal walls 43 and 44; and a storage chamber 50 for a blocking liquid 51 communicating with the pouring chamber 20 via a capillary duct 52 and partially subdivided by an internal wall 53.

References 63, 64, 65, and 66 designate sloping portions of some of the walls belonging to chambers 30, 40, and 50 respectively.

By way of example, the chambers may have the following volumes respectively: 200, 300, and 300 microliters. The capillary ducts 5, 32, 42, and 52 are at various orientations relative to the pouring chamber 20. The ducts 32 and 42 are substantially diametrically opposite each other, the duct 5 is substantially orthogonal to the above-mentioned two ducts, and the duct 52 is at an angle of substantially 45° with the duct 32.

The lid 2 has a chimney 12 located above the pouring chamber 20 and suitable for receiving a stopper 9. Throughout the storage of the container and the liquids it contains, the stopper 9 serves to close all of the orifices which open out into the pouring chamber 20 (and in particular the capillary ducts 32, 42, and 52, and the orifices 13). An air vent 28 is provided through the stopper 9. Finally, the lid 2 is provided with a closable opening 27 situated above the reaction vat, and suitable for directly inserting water or any other cleaning or flushing liquid into the reaction vat.

FIGS. 3 to 20 show a container 1 in accordance with the invention and as seen from above. Initially the container is filled with three liquids, mainly the conjugate liquid 31, the substrate liquid 41, and the blocking liquid 51. In addition, the container contains a bead 17 which is covered with antigens or antibodies depending on the reaction to be investigated. The container 1 is hermetically sealed by its lid 2 and its stopper 9 and is thus suitable for being stored prior to use.

When used, a quantity of serum 25 is inserted into the insertion receptacle 3. The serum 25 flows under gravity into the sample storage chamber 4.

The container is then placed on the periphery of a turntable to be subjected to several centrifuging operations. FIGS. 5, 7, 9, 15, and 18 illustrate centrifuging operations, with the direction of centrifugal force being indicated in each case by an arrow 29. Between two centrifuging operations, the container is capable of being rotated about its axis 19, as shown by arrows 24.

Figure 3:
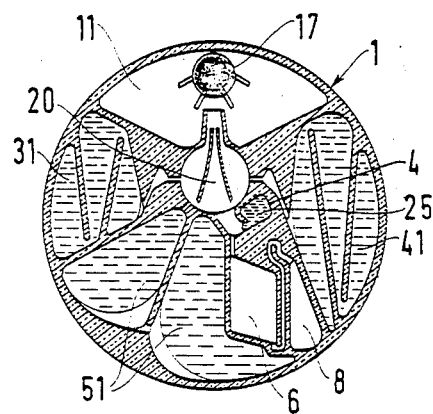
FIGS. 3 to 20 are similar views to FIG. 2 showing the various steps of the method in accordance with the invention.
Figure 4:
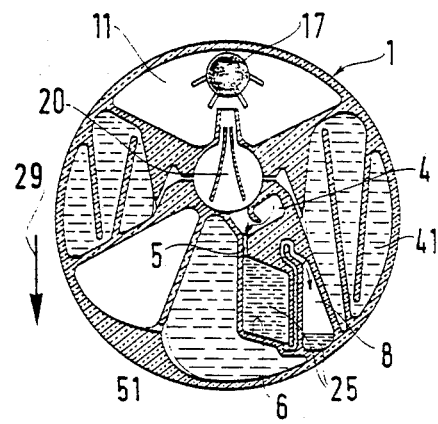
Figure 5:
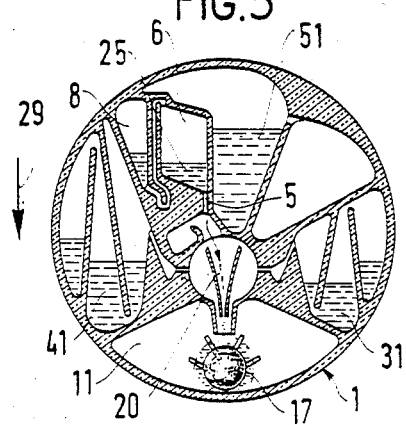
Figure 6:
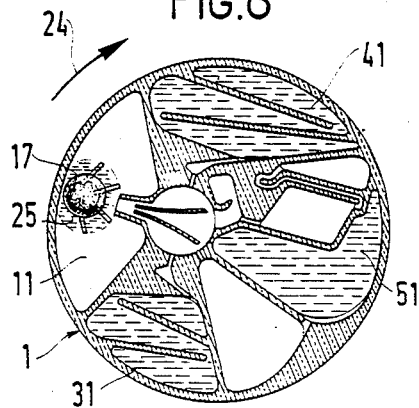
Figure 7:
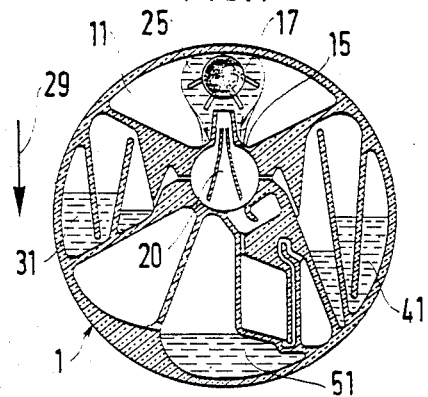

FIG. 3 shows the initial position of the container 1. During a first centrifuging operation, the serum 25 passes (see FIG. 4) from the sample storage chamber 4 via the capillary duct 5 towards the calibrated cell 6, together with its associated capillary duct 7 and overflow chamber 8. The calibrated cell 6 may have a volume of 200 microliters, for example.

The container is then rotated through 180° about its axis and is subjected to a second centrifuging operation (FIG. 5) causing the calibrated volume of serum 25 to leave the calibrated cell 6 and pass back along the duct into the pouring chamber 20 thus reaching the bead 17.

After being rotated through a further 180° (FIG. 6) and being centrifuged a third time (FIG. 7) excess serum 25 passes via the orifices 15 into the liquid drain tank.

Figure 8:
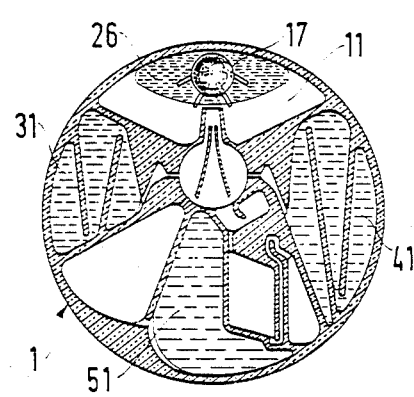
Figure 9:
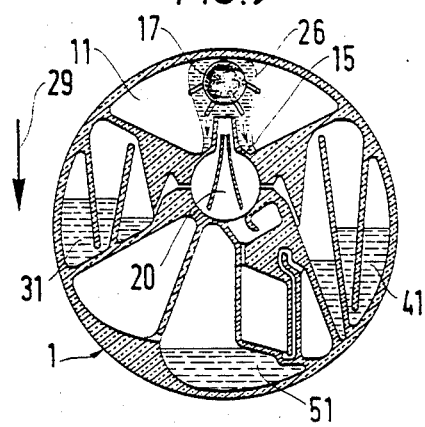

FIG. 8 shows a step in which a quantity of water 26 is inserted directly into the reaction vat 11 by means of a calibrated pipette and the opening 27 through the lid 2. As shown in FIG. 9, a fourth centrifuging operation serves to remove the excess water 26 into the liquid drain tank via the orifices 15.

Figure 10:
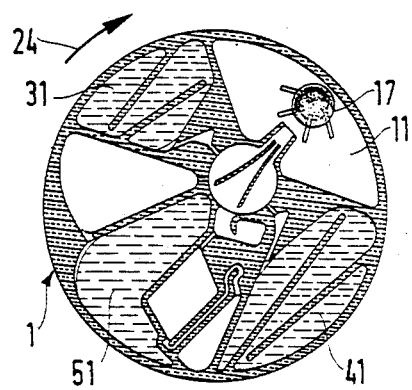
Figure 11:
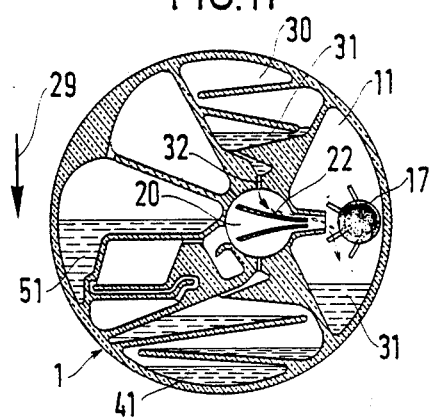
Figure 12:
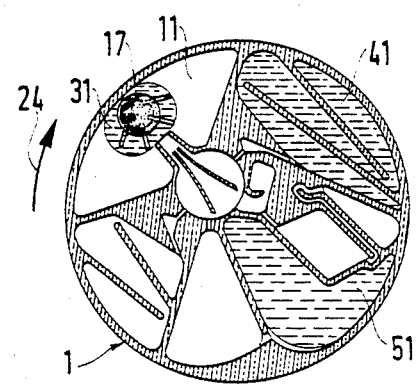
Figure 13:
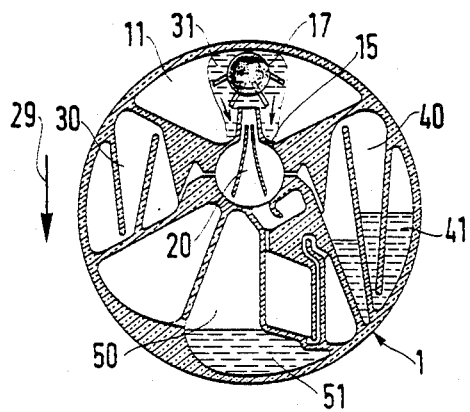

FIGS. 10 and 11 show that the container is rotated through 90° and then centrifuged. In this position the capillary duct 32 lies parallel to the direction 29 of centrifugal force. The conjugate liquid 31 in the chamber 30 thus passes during the fifth centrifuging operation via the duct 32 into the reaction vat 11. The container is again rotated through 90° (see FIG. 12) to allow the bead to be immersed in the conjugate liquid 31. A sixth centrifuging operation illustrated by FIG. 13 eliminates excess conjugate liquid 31 via the orifices 15 into the drain tank.

Figure 14:
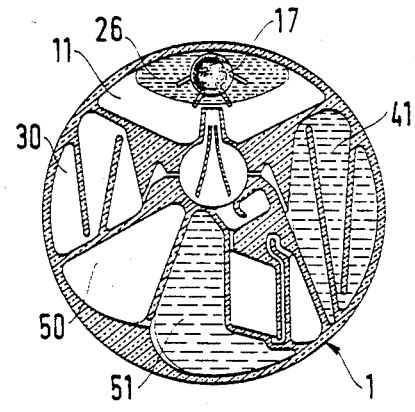
Figure 15:
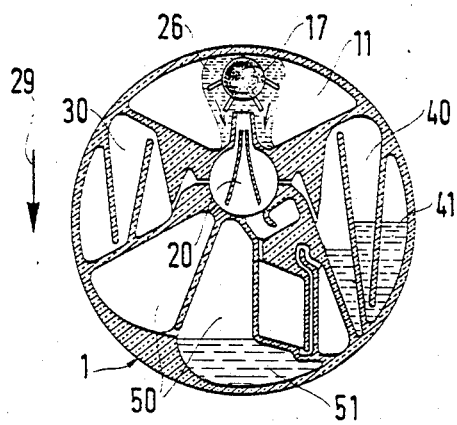
Figure 16:
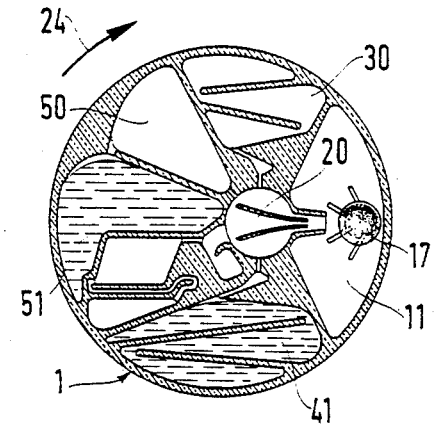
Figure 17:
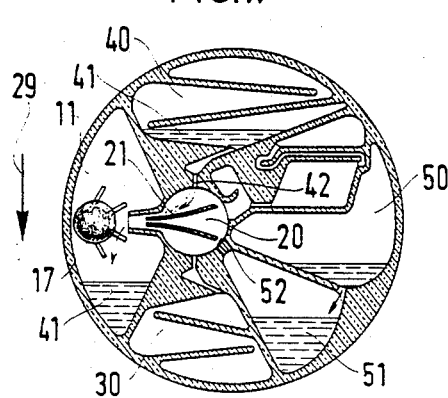

In the step illustrated in FIG. 14, a further quantity of water 26 is inserted into the reaction vat 11 via the opening 27 through the lid. A seventh centrifuging operation shown in FIG. 15 eliminates excess water after flushing via the orifices 15 into the drain tank.

The container is then rotated through 270° (FIG. 16) so that the capillary duct 42 is parallel to the direction of centrifugal force 29. An eighth centrifuging operation (FIG. 17) causes the substrate liquid 41 to pass from the chamber 40 via the capillary duct 42 into the pouring chamber 20 and thus into the reaction vat 11. Simultaneously, the blocking liquid passes into the compartment of the chamber 50 which includes the capillary duct 52.

Figure 18:
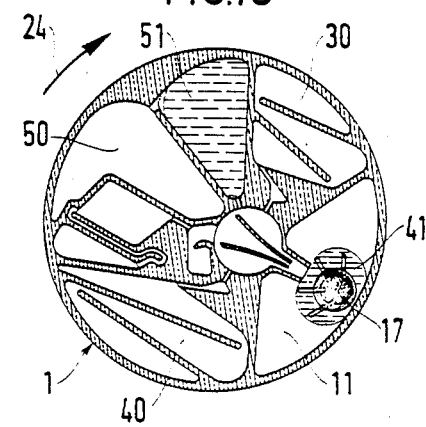
Figure 19:
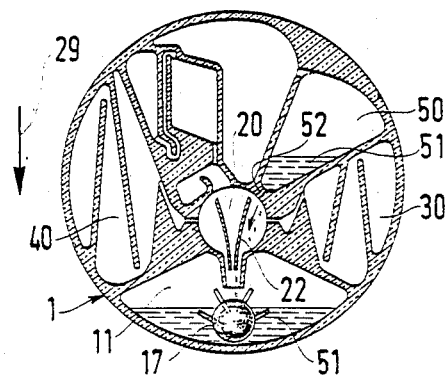

The container is again rotated through 270° (see FIG. 18). The capillary duct 52 extends sufficiently closely along the centrifugal force direction 29 for the blocking liquid 51 to pass along said duct into the pouring chamber 20 and thus into the reaction vat 11.

Figure 20:
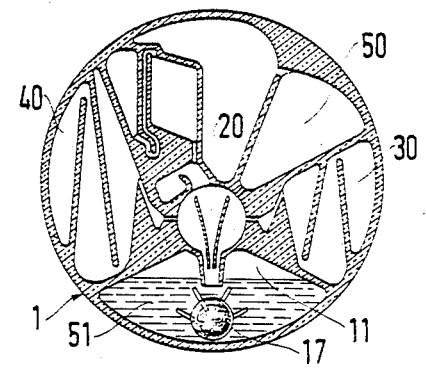

The final state is shown in FIG. 20. All of the chambers are empty and the reaction which takes place on the bead may be observed through the lid 2, for example by means of a photometer.

All of the steps of the method as described above are readily automated.

Naturally, the invention is not limited to the embodiment described above. Thus, instead of using a bead, the bead-receiving depression 16 may be directly covered with antibodies or antigens. A plurality of beads held in fixed positions in the vat could be used instead of a single bead. The blocking liquid may be constituted merely by a diluent. Without going beyond the scope of the invention, any means may be replaced by equivalent means.

I claim:

1. A method of performing biological analyses using immunological reactions on a liquid sample, the method comprising the steps of:
   providing a container which is closed by a lid, said container having compartments to define:
      a storage chamber for said liquid sample, said storage chamber being connected by a capillary duct to one end of a calibrated cell whose other end is connected via a capillary duct to an overflow chamber;
      a plurality of liquid storage chambers, for storing liquids such as a conjugate liquid, a substrate liquid, and a blocking liquid, said liquid storage chambers being disposed around a pouring chamber, said pouring chamber being connected to each of said liquid storage chambers and to said calibrated cell via respective capillary ducts extending in various directions, said pouring chamber also communicating with a reaction vat via a spout preventing liquid from returning from said reaction vat to said pouring chamber;
      a liquid drain tank communicating with said reaction vat; and
      a bead fixed in said reaction vat and suitable for being covered with antigens or antibodies;
   said lid being provided with:
      an insertion receptacle for receiving a sample and communicating directly with said sample storage chamber, said insertion receptacle being situated above said sample storage chamber; and
      a removable stopper penetrating into said pouring chamber to close the ends of said capillary ducts leading thereto; and a closable opening communicating directly with said reaction vat to enable a cleaning liquid to be inserted therein;
   means being provided for positioning said container on the periphery of a turntable in a plurality of different predetermined positions, which positions differ from one another by said container being rotated about its own axis through a given angle relative to said turntable;
   said conjugate liquid, said substrate liquid, and said blocking liquid being initially disposed in respective ones of said liquid storage chambers;
   said sample being inserted into said sample insertion receptacle, and flowing therefrom under gravity into said sample storage chamber;
   said stopper being removed;
   said container being placed on said turntable in order to perform a plurality of successive centrifuging operations, with the angular position of said container being selected each time from said predetermined angular position as a function of the orientation of the capillary duct concerned relative to the direction of centrifugal force in such a manner as to perform the following sequence of operations:
   passing said sample from said storage chamber into said calibrated cell;
   passing said sample from said calibrated cell into said reaction vat;
   eliminating surplus sample which is not fixed on said bead to said drain tank;
   inserting said flushing liquid into said reaction vat to clean said bead a first time, then eliminating said liquid to said drain tank;

inserting said conjugate liquid into said reaction vat via said pouring chamber;
eliminating surplus conjugate liquid which is not fixed on said bead into said drain tank;
inserting said flushing liquid into said reaction vat to clean said bead a second time and eliminating said liquid to said drain tank;
inserting said substrate liquid into said reaction vat via said pouring chamber;
eliminating surplus substrate liquid which is not fixed on said lead into said drain tank;
inserting said blocking liquid into said reaction vat via said pouring chamber; and
then reading the reaction on said bead by optical analysis means.

2. A method according to claim 1, wherein said predetermined positions of said container are at substantially the following angles from one another: 60°; 90°; 180°; and 270°; with said capillary ducts leading to said pouring chamber being substantially at said angles from one another.

* * * * *